US007880004B2

(12) United States Patent
Borzilleri et al.

(10) Patent No.: US 7,880,004 B2
(45) Date of Patent: Feb. 1, 2011

(54) MET KINASE INHIBITORS

(75) Inventors: Robert M. Borzilleri, New Hope, PA (US); Zhen-wei Cai, Belle Mead, NJ (US); Donna D. Wei, Belle Mead, NJ (US); John S. Tokarski, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1146 days.

(21) Appl. No.: 11/521,035

(22) Filed: Sep. 14, 2006

(65) Prior Publication Data

US 2007/0117802 A1 May 24, 2007

Related U.S. Application Data

(60) Provisional application No. 60/717,357, filed on Sep. 15, 2005.

(51) Int. Cl.
*A61K 31/444* (2006.01)
*A61K 31/437* (2006.01)
*C07D 471/04* (2006.01)
*C07D 213/64* (2006.01)

(52) U.S. Cl. .................. 546/113; 546/261; 514/300; 514/335

(58) Field of Classification Search ................. 546/113, 546/118, 119, 121, 261; 514/335, 300
See application file for complete search history.

(56) References Cited

U.S. PATENT DOCUMENTS

| 6,214,344 | B1 | 4/2001 | Schwall et al. |
| 6,429,213 | B1 | 8/2002 | Xue et al. |
| 6,858,626 | B2 | 2/2005 | Xue et al. |
| 2006/0009453 | A1 | 1/2006 | Geuns-Meyer et al. |

FOREIGN PATENT DOCUMENTS

| EP | 0 119 774 | 9/1984 |
| EP | 0 151 962 | 8/1985 |
| EP | 0 152 910 | 8/1985 |
| WO | WO00/71129 | 11/2000 |
| WO | WO01/94353 | 12/2001 |
| WO | WO02/40486 | 5/2002 |
| WO | WO03/000194 | 1/2003 |
| WO | WO03/004217 | 5/2003 |
| WO | WO03/082208 | 10/2003 |
| WO | WO03/091229 | 11/2003 |
| WO | WO2004/048386 | 6/2004 |
| WO | WO2004/048386 A2 | 6/2004 |
| WO | WO2004/048386 A3 | 6/2004 |
| WO | WO2004/054514 A2 | 7/2004 |
| WO | WO2005/021554 | 3/2005 |
| WO | WO2005/110988 | 11/2005 |
| WO | WO2006/065946 | 6/2006 |
| WO | WO 2006/116713 | 11/2006 |

OTHER PUBLICATIONS

Bunnet, J. F. et. al. "Aromatic Nucleophilic Substitution Reactions" Chemical Reviews 1951, 49, 273-412.*
Yukawa et. al. "MNDO (Modified Neglect of Diatomic Overlap) Study of the Nucleophilic Substitution Reactions of Chloropyrimidines" Chemical and Pharmaceutical Bulletin 1989, 37, 2892-2896.*
Beutner et. al. "Expedient Synthesis of 3-Alkoxymethyl- and 3-Aminomethyl-Pyrazolo[3,4-b]pyridines" Journal of Organic Chemistry 2009, 74, 789-794.*
Chioua et. al. "Synthesis and biological evaluation of 3,6-diamino-1Hpyrazolo[3,4-b]pyridine derivatives as protein kinase inhibitors" Bioorganic & Medicinal Chemistry Letters 2009, 19, 4566-4569.*
Michelotti et. al. "Two classes of p38a MAP kinase inhibitors having a common diphenylether core but exhibiting divergent binding modes" Bioorganic & Medicinal Chemistry Letters 2005, 15, 5274-5279.*
Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Miyazaki et. al. "Design and effective synthesis of novel templates, 3,7-diphenyl-4- amino-thieno and furo-[3,2-c]pyridines as protein kinase inhibitors and in vitro evaluation targeting angiogenetic kinases" Bioorganic & Medicinal Chemistry Letters 2007, 17, 250-254.*
Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*

(Continued)

*Primary Examiner*—Janet L Andres
*Assistant Examiner*—David K O'Dell
(74) *Attorney, Agent, or Firm*—Gary D. Greenblatt; Maureen S. Gibbons

(57) ABSTRACT

The invention is directed to compounds that are useful for the treatment of cancer having the following Formula:

16 Claims, No Drawings

OTHER PUBLICATIONS

Mulvihill et. al. "1,3-Disubstituted-imidazo[1,5-a]pyrazines as insulin-like growth-factor-I receptor (IGF-IR) inhibitors" Bioorganic & Medicinal Chemistry Letters 2007, 17, 1091-1097.*

Kim e.t al. "Pyrrolopyridine-Pyridone Based Inhibitors Based Inhibitors of Met Kinase: Synthesis, X-ray Crystallographic Analysis, and Biological Activities." Journal of Medicinal Chemistry, 2008, vol. 51, No. 17 5330-5341.*

Bardelli, A. et al., "Concomitant activation of pathways downstream of Grb2 and PI3-kinase is required for *MET*-mediated metastasis", Oncogene, vol. 18, pp. 1139-1146.

Barker, J. et al., "Thienopyridines. Part 7. Some Electrophilic Substitution Reactions of Thieno[2,3-b]—and—[3,2-b] pyridines Isosteres of 4-Oxygenated and 2,4-Dioxygenated Quinolines", J. Chem. Research, vol. 4, pp. 122-123 (1986).

Bottaro, D. et al., "Identification of the Hepatocyte Growth Factor Receptor as the *c-met* Proto-Oncogene Product", Science, vol. 251, pp. 802-804 (1991).

Bussolino, F. et al., "Hepatocyte Growth Factor is a Potent Angiogenic Factor which Stimulates Endothelial Cell Motility and Growth", The J. of Cell Biology, vol. 119, pp. 629-641 (1992).

Camp, R. et al., "*Met* Expression is Associated with Poor Outcome in Patients with Axillary Lymph Node Negative Breast Carcinoma", Cancer, vol. 86(11), pp. 2259-2265 (1999).

Cañibano, V. et al., "Mild Regioselective Halogenation of Activated Pyridines with *N*-Bromosuccinimide", Synthesis, vol. 14, pp. 2175-2179 (2001).

Christensen, J. et al., "A Selective Small Molecule Inhibitor of c-Met Kinase Inhibits c-Met-Dependent Phenotypes in Vitro and Exhibits Cytoreductive Antitumor Activity in Vivo", Cancer Research, vol. 63, pp. 7345-7355 (2003).

Cooper, C. et al., "Amplification and overexpression of the *met* gene in spontaneously transformed NIH3T3 mouse fibroblasts", The EMBO Journal, vol. 5(10), pp. 2623-2628 (1986).

Di Renzo, M. et al., "Overexpression and Amplification of the Met/HGF Receptor Gene during the Progression of Colorectal Cancer", Clinical Cancer Research, vol. 1, pp. 147-154 (1995).

Dorn, H. et al., "Eindeutige Synthese des 4,7-Dihydro-4-oxo-1 H-pyrazolo[3,4-b] pyridins-Bemerkungen zur(N-C)—Umlagerung von (2-Alkoxycarbonyl-vinyl-amino) pyrazolen", Journal f. prakt. Chemie, vol. 324(4), pp. 557-562 (1982).

Furge, K. et al., "Met receptor tyrosine kinase: enhanced signaling through adapter proteins", Oncogene, vol. 19, pp. 5582-5589 (2000).

Gual, P. et al., "Sustained recruitment of phospholipase C-γ to Gab1 is required for HGF-induced branching tubulogenesis", Oncogene, vol. 19, pp. 1509-1518 (2000).

Hunt, J. et al., "Discovery of the Pyrrolo[2,1-*f*] [1,2,4] triazine Nucleus as a New Kinase Inhibitor Template", J. Med. Chem., vol. 47, pp. 4054-4059 (2004).

Itoh, T. et al., "Studies on the Chemical Synthesis of Potential Antimetabolites.30. Regioselective Introduction of a Chlorine Atom into the Imidazo [4,5-*b*] pyridine Nucleus (1)", J. Heterocyclic Chem., vol. 19, pp. 513-517 (1982).

Jiang, W. et al., "Reduction of Stromal Fibroblast-induced Mammary Tumor Growth, by Retroviral Ribozyme Transgenes to Hepatocyte Growth Factor/Scatter Factor and its Receptor, c-MET", Clinical Cancer Research, vol. 9, pp. 4274-4281 (2003).

Kenworthy, P. et al., "The presence of scatter factor in patients with metastatic spread to the pleura", Br. J. Cancer, vol. 66, pp. 243-247 (1992).

Kubo, K. et al., "Novel Potent Orally Active Selective VEGFR-2 Tyrosine Kinase Inhibitors: Synthesis, Structure-Activity Relationships, and Antitumor Activities of N-Phenyl-N- {4-(4-quinolyloxy)phenyl} ureas", J. Med. Chem., vol. 48, pp. 1359-1366 (2005).

Lai, J. et al., "Involvement of Focal Adhesion Kinase in Hepatocyte Growth Factor-induced Scatter of Madin-Darby Canine Kidney Cells", The J. of Biological Chemistry, vol. 275(11), pp. 7474-7480 (2000).

Lee, J. et al., "A novel germ line juxtamembrane *Met* mutation in human gastric cancer", Oncogene, vol. 19, pp. 4947-4953 (2000).

Lubensky, I. et al., "Hereditary and Sporadic Papillary Renal Carcinomas with *c-met* Mutations Share a Distinct Morphological Phenotype", American J. of Pathology, vol. 155(2), pp. 517-526 (1999).

Masuya, D. et al., "The tumour-stromal interaction between intratumoral c-Met and stromal hepatocyte growth factor associated with tumour growth and prognosis in non-small-cell lung cancer patients", British J. of Cancer, vol. 90, pp. 1555-1562 (2004).

Matsumoto, K. et al., Hepatocyte Growth Factor: Molecular Structure, Roles in Liver Regeneration, and Other Biological Functions, Critical Reviews in Oncogenesis, vol. 3 (1,2), pp. 27-54 (1992).

Montesano, R. et al., "Identification of a Fibroblast-Derived Epithelial Morphogen as Hepatocyte Growth Factor", Cell, vol. 67, pp. 901-908 (1991).

Park, M. et al., "Sequence of *MET* protooncogene cDNA has features characteristic of the tyrosine kinase family of growth-factor receptors", PNAS, vol. 84, pp. 6379-6383 (1987).

Rong, S. et al., "Met Expression and Sarcoma Tumorigenicity", Cancer Research, vol. 53, pp. 5355-5360 (1993).

Rong, S. et al., "Met Proto-oncogene Product is Overexpressed in Tumors of p53-deficient Mice and Tumors of Li-Fraumeni Patients", Cancer Research, vol. 55, pp. 1963-1970 (1995).

Sachs, M. et al., "Essential Role of Gab1 for Signaling by the c-Met Receptor in Vivo", The J. of Cell Biology, vol. 150, pp. 1375-1384 (2000).

Sanghvi, Y. et al., "Synthesis and Biological Evaluation of Certain C-4 Substituted Pyrazolo [3,4-*b*] pyridine Nucleosides", J. Med. Chem., vol. 32, pp. 945-951 (1989).

Scarpino, S. et al., "Hepatocyte Growth Factor (HGF) Stimulates Tumour Invasiveness in Papillary Carcinoma of the Thyroid", Journal of Pathology, vol. 189, pp. 570-575 (1999).

Schaeper, U. et al., "Coupling of Gab1 to c-Met, Grb2, and Shp2 Mediates Biological Responses", vol. 149(7), pp. 1419-1432 (2000).

Soman, N. et al., "The *TPR-MET* oncogenic rearrangement is present and expressed in human gastric carcinoma and precursor lesions", PNAS, vol. 88, pp. 4892-4896 (1991).

Sonnenberg, E. et al., "Scatter Factor/Hepatocyte Growth Factor and Its Receptor, the c-met Tyrosine Kinase, Can Mediate a Signal Exchange between Mesenchyme and Epithelia during Mouse Development", The J. of Cell Biology, vol. 123(1), pp. 223-235 (1993).

Stabile, L., et al., "Inhibition of human non-small cell lung tumors by a c-Met antisense/U6 expression plasmid strategy", Gene Therapy, vol. 11, pp. 325-335 (2004).

Stella, M. et al., "HGF: a multifunctional growth factor controlling cell scattering", The International J. of Biochemistry & Cell Biology, vol. 31, pp. 1357-1362 (1999).

Stoker, M. et al., "Scatter factor is a fibroblast-derived modulator of epithelial cell mobility", Nature, vol. 327, pp. 239-242 (1987).

Stuart, K. et al., "Hepatocyte growth factor/scatter factor-induced intracellular signalling", Int. J. Exp. Path., vol. 81, pp. 17-30 (2000).

Takayama, H. et al., "Diverse tumorigenesis associated with aberrant development in mice overexpressing hepatocyte growth factor/scatter factor", PNAS, vol. 94, pp. 701-706 (1997).

Tanimura, S. et al., "Activation of the 41/43 kDa mitogen-activated protein kinase signaling pathway is required for hepatocyte growth factor-induced cell scattering", Oncogene, vol. 17, pp. 57-65 (1998).

Tedder, M. et al., "Structure-based design, synthesis, and antimicrobial activity of purine derived SAH/MTA nucleosidase inhibitors", Bioorganic & Medicinal Chemistry Letters, vol. 14, pp. 3165-3168 (2004).

Temple, Jr. C. et al., "Preparation and Properties of Some Isomeric v-Triazolopyridines,. 1- and 3-Deaza-8-azapurines", J. Org. Chem., vol. 37(23), pp. 3601-3604 (1972).

Thibault, C. et al., "Concise and Efficient Synthesis of 4-Fluoro-1*H*-pyrrolo [2,3-*b*] pyridine", Organic Letters, vol. 5(26), pp. 5023-5025 (2003).

Zhang, Z. et al., "A General Method for the Preparation of 4-and 6-Azaindoles", J. Org. Chem., vol. 67, pp. 2345-2347 (2002).

U.S. Office Action in U.S. Appl. No. 11/111,144 dated Mar. 3, 2008.

* cited by examiner

MET KINASE INHIBITORS

RELATED APPLICATION

This application claims priority benefit under Title 35 §119(e) of U.S. provisional Application No. 60/717,357, filed Sep. 15, 2005, the contents of which are herein incorporated by reference.

FIELD OF THE INVENTION

This invention relates to compounds that inhibit the protein tyrosine kinase activity of growth factor receptors such as c-Met, thereby making them useful as anti-cancer agents. The pharmaceutical compositions that comprise these compounds are also useful in the treatment of diseases, other than cancer, which are associated with signal transduction pathways operating through growth factor and anti-angiogenesis receptors such as c-Met.

BACKGROUND OF THE INVENTION

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235, 1993; Matsumato et al., *Crit. Rev. Oncog.* 3:27-54, 1992; and Stoker et al., *Nature* 327:239-242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901-908, 1991), and promotion of invasion (Stella et al., *Int. J. Biochem. Cell Biol.* 12:1357-62, 1999 and Stuart et al., *Int. J. Exp. Path.* 81:17-30, 2000), all critical processes underlying metastasis. HGF has also been reported to promote angiogenesis (Bussolino et al., *J. Cell Biol.* 119:629-641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA* 84:6379-83, 1987 and Bottaro et al., *Science* 251:8024, 1991). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582-9, 2000). These include the p85 subunit of the PI3-kinase, phospholipase Cγ (Gaul et al., *Oncogene* 19:1509-18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149:1419-32, 2000; Bardelli, et al., *Oncogene* 18:1139-46, 1999 and Sachs et al., *J. Cell Biol.* 150:1375-84, 2000). Activation of other signaling molecules has been reported in HGF stimulated cells, most notably Ras, MAP kinases, STATs, ERK-1, -2 and FAK (Tanimura et al., *Oncogene* 17:57-65, 1998; Lai et al., *J. Biol. Chem.* 275:7474-80 2000 and Furge et al., *Oncogene* 19:5582-9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology*, 155:517-26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.*, 63:7345-55, 2003; Lee et al., *Oncogene*, 19:4947-53, 2000 and Direnzo et al., *Clin. Cancer Res.*, 1:147-54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res.* 55:1963-1970, 1995; Rong et al., *Cancer Res.* 53:5355-5360, 1993; Kenworthy et al., *Br. J. Cancer* 66:243-247, 1992 and Scarpino et al. *J. Pathology* 189:570-575, 1999). TPR-Met (an activated form similar to BCR/Ab1 in CML) has been described and identified in human gastric carcinoma (PNAS 88:4892-6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259-65 1999 and Masuya et al., *Br. J. Cancer,* 90:1555-62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS,* 94:701-6, 1997) and an amplified/overexpressed Met spontaneously transforms NIH-3T3 cells (Cooper et al., *EMBO J.,* 5:2623-8, 1986).

Biological agents, such as ribozymes, antibodies and antisense RNA targeting either HGF or Met have been shown to inhibit tumorogenesis (Stabile et al., *Gene Therapy,* 11:325-35, 2004, Jiang et al., *Clin. Cancer Res,* 9:4274-81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

SUMMARY

The present invention is directed to compounds that are useful for treating cancer. More specifically, the present invention is directed to compounds having the following Formula I or II:

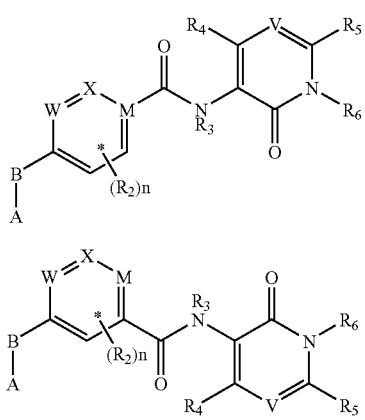

wherein

W, M and X are each independently C or N;

each $R^2$ is independently, H, halogen, cyano, $NO_2$, $OR^7$, $NR^8R^9$, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, aryalkyl, substituted arylalkyl, heterocycloalkyl, or substituted heterocycloalkyl;

n is 1 to 4;

$R^3$, $R^6$, $R^7$, $R^8$, $R^9$ and $R^{11}$ are independently, H, $C_1$ to $C_6$ alkyl, substituted $C_1$ to $C_6$ alkyl, $C_3$ to $C_7$ cycloalkyl, substituted $C_3$ to $C_7$ cycloalkyl, —C(O)$R^{17}$, —S(O)$_2R^{17}$, $C_5$ to $C_{14}$ aryl, substituted $C_6$ to $C_{14}$ aryl, $C_5$ to $C_{14}$ heteroaryl, substituted $C_5$ to $C_{14}$ heteroaryl, arylalkyl, substituted arylalkyl, heteroarylalkyl, substituted heteroarylalkyl, heterocycloalkyl, substituted heterocycloalkyl, heterocycloalkylalkyl or substituted heterocycloalkylalkyl;

V is N or —$CR^{10}$;

B is O, —$NR^{11}$, S, SO, $SO_2$, or —$CR^{12}R^{13}$;

$R^4$, $R^5$, and $R^{10}$ are independently, H, halogen, halogenated alkyl, $NO_2$, cyano, —$OR^{14}$, $NR^{15}R^{16}$, $CO_2R^{17}$, $C(O)NR^{15}R^{16}$, $SO_2R^{17}$, $SO_2NR^{15}R^{16}$, $NR^{18}SO_2R^{17}$, $NR^{18}C(O)R^{19}$, $NR^{18}CO_2R^{19}$, —CO(CH$_2$)$_mR^{20}$; —CONH(CH$_2$)$_mR^{21}$, —$SR^{22}$, —$SOR^{23}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^{12}$ and $R^{13}$ are independently H, halo, alkyl, substituted alkyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms;

$R^{14}$, $R^{15}$, $R^{16}$, $R^{17}$, $R^{18}$, $R^{19}$, $R^{20}$, $R^{21}$, $R^{22}$ and $R^{23}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl; and A is a 5 to 10 membered nitrogen containing heterocycle selected from the group consisting of:

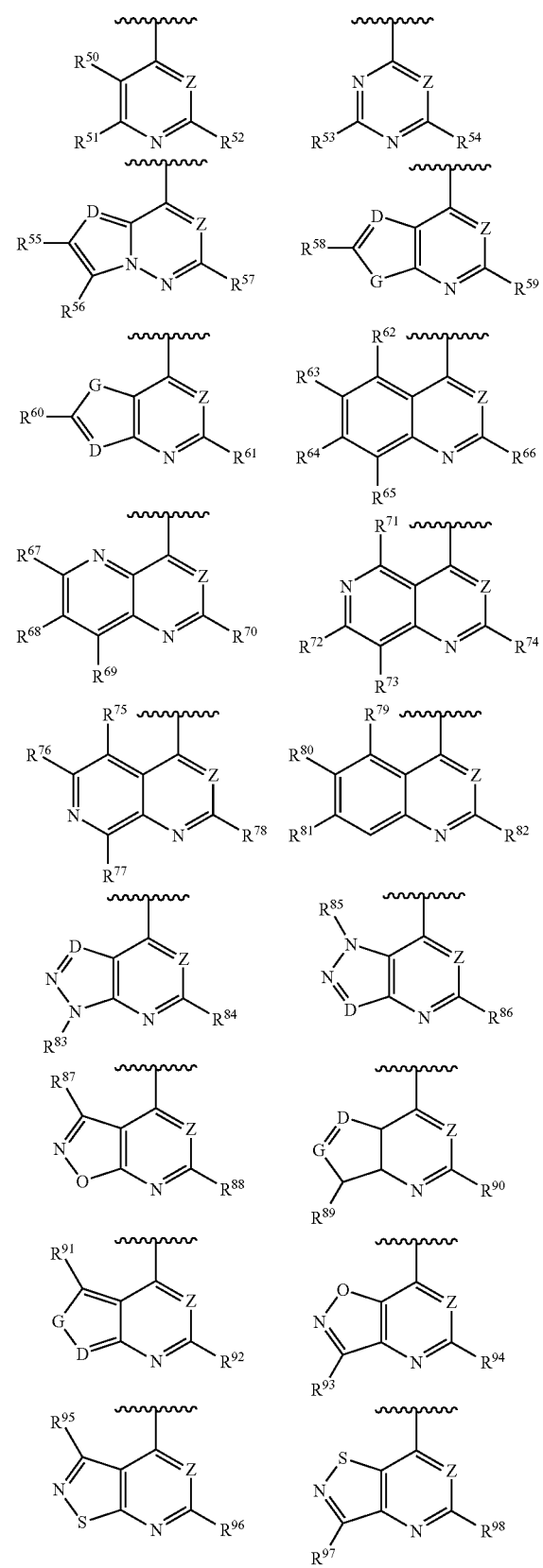

-continued

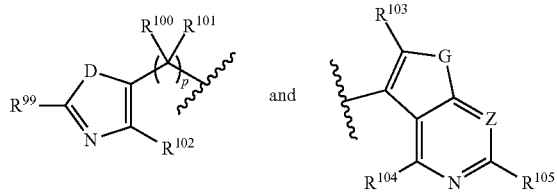

wherein $R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}, R^{68}, R^{69}, R^{70}, R^{71}, R^{72}, R^{73}, R^{74}, R^{75}, R^{76}, R^{77}, R^{78}, R^{79}, R^{80}, R^{81}, R^{82}, R^{84}, R^{86}, R^{87}, R^{88}, R^{89}, R^{90}, R^{91}, R^{92}, R^{93}, R^{94}, R^{95}, R^{96}, R^{97}, R^{98}, R^{99}, R^{102}, R^{103}, R^{104}, R^{105}, R^{107}$ and $R^{108}$ are each independently H, halogen, halogenated alkyl, $NO_2$, cyano, —$OR^{109}$, $NR^{110}R^{111}$, $CO_2R^{112}$, $C(O)NR^{113}R^{114}$, $SO_2R^{115}$, $SO_2NR^{116}R^{117}$, $NR^{118}SO_2R^{119}$, $NR^{120}C(O)R^{121}$, $NR^{122}CO_2R^{123}$, —$CO(CH_2)_mR^{124}$; —$CONH(CH_2)_mR^{125}$, —$SR^{126}$, —$SOR^{127}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^{83}$ and $R^{85}$, are each independently H, $C_1$ to $C_6$ alkyl, haloalkyl, —$CO_2R^{128}$, $SO_2R^{129}$, —$CO(CH_2)_mR^{130}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, hydroxyalkyl, aryl, substituted aryl, heteroaryl, substituted heteroaryl, arylalkyl, substituted arylalkyl, or heterocycloalkyl;

$R^{100}$ and $R^{101}$ are each independently are independently selected from H, halogen, alkyl, substituted alkyl, cycloalkyl, substituted cycloalkyl, aryl, substituted aryl, heteroaryl, substituted heteroaryl, heterocycloalkyl, or substituted heterocycloalkyl, or taken together to form a carbocyclic or heterocyclic ring of 3 to 8 atoms;

m is 0 to 4;

p is 0 to 2;

G is O, S, or $NR^{106}$;

D is $CR^{107}$ or N;

Z is N or $CR^{108}$; and $R^{106}, R^{109}, R^{110}, R^{112}, R^{113}, R^{114}, R^{115}, R^{116}, R^{117}, R^{118}, R^{119}, R^{120}, R^{121}, R^{122}, R^{123}, R^{124}, R^{125}, R^{127}, R^{129}$ and $R^{130}$ are independently selected from H, alkyl, substituted alkyl, cycloalkyl, substituted cycloalkyl, acyl, sulfonyl, aryl, substituted aryl, arylalkyl, substituted arylalkyl, heteroaryl, substituted heteroaryl, heterocycloalkyl, or substituted heterocycloalkyl.

According to one embodiment of the present invention, compounds having the following Formula III, or salts thereof, are provided:

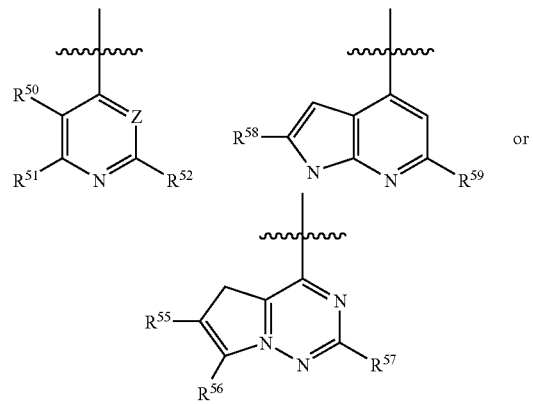

wherein
X is C or N;
B is O, S or —NH;
each $R^2$ is independently H or halo;
$R^6$ is an optionally substituted phenyl, preferably fluorophenyl;
A is:

wherein
Z is CH or N;
$R^{50}, R^{51}, R^{52}, R^{55}, R^{56}, R^{57}, R^{58}$, and $R^{59}$ are each independently H, halogen, halogenated alkyl, $NO_2$, cyano, —$OR^{109}$, $NR^{110}R^{111}$, $CO_2R^{112}$, $C(O)NR^{113}R^{114}$, $SO_2R^{115}$, $SO_2NR^{116}R^{117}$, $NR^{118}SO_2R^{119}$, $NR^{120}C(O)R^{121}$, $NR^{122}CO_2R^{123}$, —$CO(CH_2)_mR^{124}$; —$CONH(CH_2)_mR^{125}$, —$SR^{126}$, —$SOR^{127}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl; and $R^{109}, R^{110}, R^{111}, R^{112}, R^{113}, R^{114}, R^{115}, R^{116}, R^{117}, R^{118}, R^{119}, R^{120}, R^{121}, R^{122}, R^{123}, R^{124}, R^{125}, R^{126}$, and $R^{127}$ are each independently H, alkyl, substituted alkyl, cycloalkyl, substituted cycloalkyl, acyl, sulfonyl, aryl, substituted aryl, arylalkyl, substituted arylalkyl, heteroaryl, substituted heteroaryl, heterocycloalkyl, or substituted heterocycloalkyl.

According to one embodiment of the present invention, a compound is provided having Formula III or a salt thereof wherein $R^6$ is fluorophenyl; $R^3$ is H; each $R^{50}, R^{52}, R^{55}, R^{56}, R^{57}, R^{58}$, and $R^{59}$ is H; and $R^{51}$ is H or amino.

In some embodiments of the present invention, methods for treating cancer in a patient are provided, wherein the cancer is dependent upon Met activation and the Met activation is regulated by gene amplification, an activated Met mutation and/or HGF stimulation, comprising administering to the patient a therapeutically effective amount of a compound having Formula I, II, or III, as defined above, in a pharmaceutically acceptable carrier, optionally comprising the administration of at least one additional anticancer agent.

According to one embodiment of the present invention, pharmaceutical compositions are provided comprising a compound having Formula I or II, or a salt thereof, as defined above, in a pharmaceutically acceptable carrier.

DETAILED DESCRIPTION OF THE INVENTION

The present invention is directed to compounds that are useful for treating cancer. More specifically, the present invention is directed to compounds having the following Formula I:

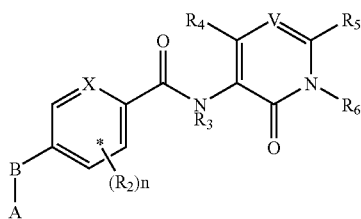

or a salt thereof:

wherein each $R^2$ is independently, H, halogen, cyano, $NO_2$, $OR^7$, $NR^8R^9$, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, aryalkyl, substituted arylalkyl, heterocycloalkyl, or substituted heterocycloalkyl;

n is 1 to 4;

X is C or N;

$R^3$, $R^6$, $R^7$, $R^8$, $R^9$ and $R^{11}$ are independently, H, $C_1$ to $C_6$ alkyl, substituted $C_1$ to $C_6$ alkyl, $C_3$ to $C_7$ cycloalkyl, substituted $C_3$ to $C_7$ cycloalkyl, —C(O)$R^{17}$, —S(O)$_2R^{17}$, $C_5$ to $C_{14}$ aryl, substituted $C_6$ to $C_{14}$ aryl, $C_5$ to $C_{14}$ heteroaryl, substituted $C_5$ to $C_{14}$ heteroaryl, arylalkyl, substituted arylalkyl, heteroarylalkyl, substituted heteroarylalkyl, heterocycloalkyl, substituted heterocycloalkyl, heterocycloalkylalkyl or substituted heterocycloalkylalkyl;

V is N or —$CR^{10}$;

B is O, —$NR^{11}$, S, SO, $SO_2$, or —$CR^{12}R^{13}$;

$R^4$, $R^5$, and $R^{10}$ are independently, H, halogen, halogenated alkyl, $NO_2$, cyano, —$OR^{14}$, $NR^{15}R^{16}$, $CO_2R^{17}$, $C(O)NR^{15}R^{16}$, $SO_2R^{17}$, $SO_2NR^{15}R^{16}$, $NR^{18}SO_2R^{17}$, $NR^{18}C(O)R^{19}$, $NR^{18}CO_2R^{19}$, —$CO(CH_2)_mR^{20}$; —$CONH(CH_2)_mR^{21}$, —$SR^{22}$, —$SOR^{23}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^{12}$ and $R^{13}$ are independently H, halo, alkyl, substituted alkyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms;

$R^{14}$, $R^{15}$, $R^{16}$, $R^{17}$, $R^{18}$, $R^{19}$, $R^{20}$, $R^{21}$, $R^{22}$ and $R^{23}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl; and A is a 5 to 10 membered nitrogen containing heterocycle selected from the group consisting of:

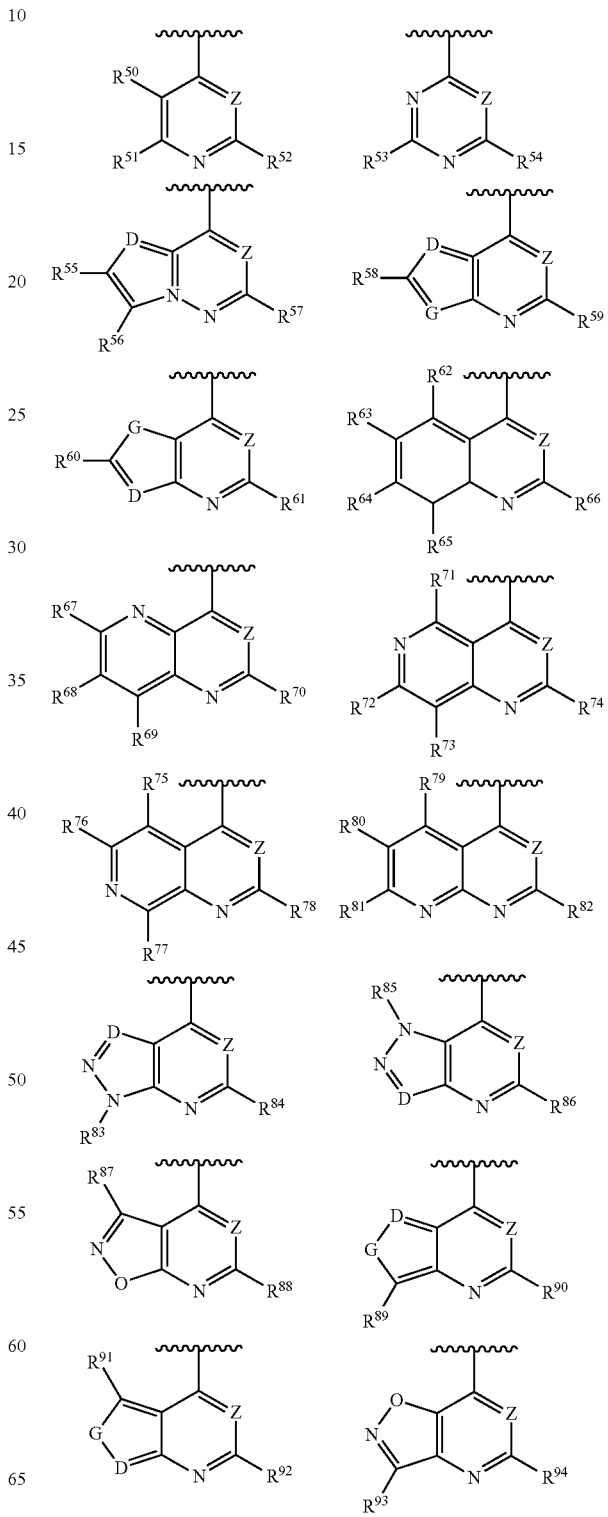

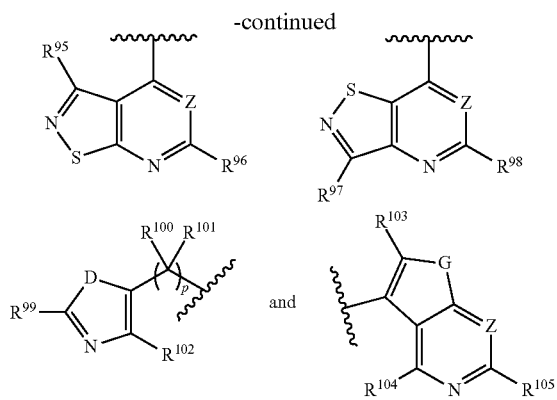

wherein
$R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$, $R^{80}$ $R^{81}$, $R^{82}$, $R^{84}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$, $R^{98}$, $R^{99}$, $R^{102}$, $R^{103}$, $R^{104}$, $R^{105}$, $R^{107}$ and $R^{108}$ are each independently H, halogen, halogenated alkyl, $NO_2$, cyano, —$OR^{109}$, $NR^{110}R^{111}$, $CO_2R^{112}$, $C(O)NR^{113}R^{114}$, $SO_2R^{115}$, $SO_2NR^{116}R^{117}$, $NR^{118}SO_2R^{119}$, $NR120C(O)R^{121}$, —$CO(CH_2)_mR^{124}$; —$CONH(CH_2)_mR^{125}$, —$SR^{126}$, —$SOR^{127}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^{83}$ and $R^{85}$, are each independently H, $C_1$ to $C_6$ alkyl, haloalkyl, —$CO_2R^{128}$ $SO_2R^{129}$, —$CO(CH_2)_mR^{130}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, hydroxyalkyl, aryl, substituted aryl, heteroaryl, substituted heteroaryl, arylalkyl, substituted arylalkyl, or heterocycloalkyl;

$R^{100}$ and $R^{101}$ are each independently are independently selected from H, halogen, alkyl, substituted alkyl, cycloalkyl, substituted cycloalkyl, aryl, substituted aryl, heteroaryl, substituted heteroaryl, heterocycloalkyl, or substituted heterocycloalkyl, or taken together to form a carbocyclic or heterocyclic ring of 3 to 8 atoms;

m is 0 to 4;
p is 0 to 2;
G is O, S, or $NR^{106}$;
D is $CR^{107}$ or N;
Z is N or $CR^{108}$; and
$R^{106}$, $R^{109}$, $R^{110}$, $R^{111}$, $R^{112}$, $R^{113}$, $R^{114}$, $R^{115}$, $R^{116}$, $R^{117}$, $R^{118}$, $R^{119}$, $R^{120}$, $R^{121}$, $R^{122}$, $R^{123}$, $R^{124}$, $R^{125}$, $R^{126}$, $R^{127}$, $R^{128}$, $R^{129}$ and $R^{130}$ are independently selected from H, alkyl, substituted alkyl, cycloalkyl, substituted cycloalkyl, acyl, sulfonyl, aryl, substituted aryl, arylalkyl, substituted arylalkyl, heteroaryl, substituted heteroaryl, heterocycloalkyl, or substituted heterocycloalkyl.

According to one embodiment of the present invention, compounds have the Formula I or a salt thereof, wherein B is O, S or —$NR^8$; and $R^2$, $R^3$ and $R^5$ are each H.

According to one embodiment of the present invention, compounds have the Formula I or a salt thereof wherein X is C and each $R^2$ is H or halo.

According to one embodiment of the present invention, compounds have the Formula I or a salt thereof wherein each $R^2$ is H or F.

According to one embodiment of the present invention, compounds have the Formula I or a salt thereof wherein $R^6$ is an optionally substituted phenyl.

According to one embodiment of the present invention, compounds have the Formula I or a salt thereof wherein said substituent is a halo.

According to one embodiment of the present invention, compounds have the Formula I or a salt thereof wherein said substituent is a F.

According to one embodiment of the present invention, compounds have the Formula I or a salt thereof wherein X and V are C.

According to one embodiment of the present invention, compounds have the Formula I or a salt thereof wherein X is N.

According to one embodiment of the present invention, compounds have the Formula I or a salt thereof wherein A is an optionally substituted pyrrolopyridine or an optionally substituted pyridine.

According to one embodiment of the present invention, compounds have the Formula I or a salt thereof wherein A is an aminopyridine.

According to one embodiment of the present invention, compounds having the Formula II, including salts thereor, are provided:

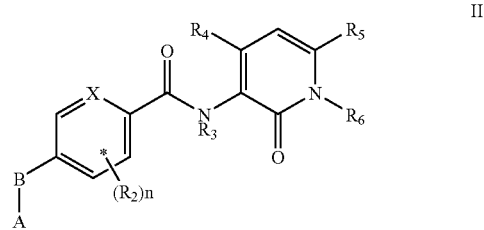

wherein
X is —$CR_2$ or N;
B is O, S or —NH;
each $R^2$ is independently H or halo;
n is 1 to 4;
$R^6$ is an optionally substituted phenyl, preferably fluorophenyl;
A is:

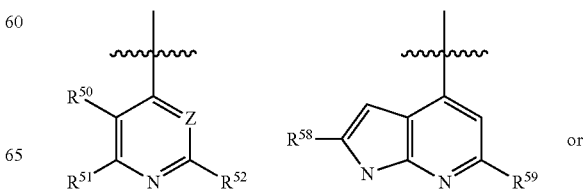

-continued

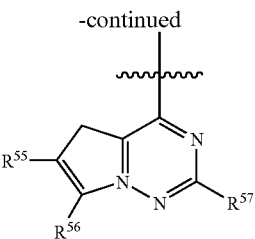

wherein

Z is CH or N;

$R^{50}$, $R^{51}$, $R^{52}$, $R^{55}$, $R^{56}$, $R^{57}$, $R^{58}$, and $R^{59}$ are each independently H, halogen, halogenated alkyl, $NO_2$, cyano, —$OR^{109}$, $NR^{110}R^{111}$, $CO_2R^{112}$, $C(O)NR^{113}R^{114}$, $SO_2R^{115}$, $SO_2NR^{116}R^{117}$, $NR^{118}SO_2R^{119}$, $NR^{120}C(O)R^{121}$, $NR^{122}CO_2R^{123}$, —$CO(CH_2)_mR^{124}$; —$CONH(CH_2)_mR^{125}$, —$SR^{126}$, —$SOR^{127}$, alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl; and $R^{109}$, $R^{119}$, $R^{111}$, $R^{112}$, $R^{113}$, $R^{114}$, $R^{115}$, $R^{116}$, $R^{117}$, $R^{118}$, $R^{119}$, $R^{120}$, $R^{121}$, $R^{122}$, $R^{123}$, $R^{124}$, $R^{125}$, $R^{126}$, and $R^{127}$ are each independently H, alkyl, substituted alkyl, cycloalkyl, substituted cycloalkyl, acyl, sulfonyl, aryl, substituted aryl, arylalkyl, substituted arylalkyl, heteroaryl, substituted heteroaryl, heterocycloalkyl, or substituted heterocycloalkyl.

According to one embodiment of the present invention, a compound is provided having Formula m wherein, wherein $R^6$ is fluorophenyl; $R^3$ is H; each $R^{50}$, $R^{52}$, $R^{55}$, $R^{56}$, $R^{57}$, $R^{58}$, and $R^{59}$ is H; and $R^{51}$ is H or amino.

In some embodiments of the present invention, methods for treating cancer in a patient are provided, wherein the cancer is dependent upon Met activation and the Met activation is regulated by gene amplification, an activated Met mutation and/or HGF stimulation, comprising administering to the patient a therapeutically effective amount of a compound having Formula I, II or III, as defined above, in a pharmaceutically acceptable carrier, optionally comprising the administration of at least one additional anticancer agent.

Specifically, the compounds of Formulae I, II and III are useful in the treatment of a variety of cancers, most specifically, those cancers that are dependent upon Met activation. Met activation may be regulated by gene amplification, mutation(s) and/or HGF stimulation in which HGF is provided by either the tumor (autocrine) or host (paracrine) tissues. Thus, the present invention is also directed to methods of treating cancers such as the following bladder breast, colorectal, gastric, head and neck, kidney, liver, lung, ovarian, pancreas/gall bladder, prostate, thyroid, osteosarcoma, rhabdomyosarcoma, MFH/fibrosarcoma, glioblastomas/astrocytomas, melanoma, and mesothelioma.

According to one embodiment of the present invention, pharmaceutical compositions are provided comprising a compound having Formula I, II, or III, as defined above, in a pharmaceutically acceptable carrier.

DEFINITIONS

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. Preferred alkyl groups have from 1 to 6 carbon atoms. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Alkyl groups may be substituted with substituents selected from the following: alkyl, aryl, aryloxy, —CN, halo (such as F, Cl, Br, I), haloalkyl (such as $CCl_3$ or $CF_3$), alkoxy, alkylthio, hydroxy, carboxy (—COOH), alkyloxycarbonyl (—C(O)nR), alkylcarbonyloxy (—OCOR), amino (—NR'R"), carbamoyl (—NHCOOR— or —OCONHR—), urea (—NHCONHR—) or thiol (—SH).

The term "alkenyl" herein alone or as part of another group refers to a hydrocarbon radical straight, branched or cyclic, containing from 2 to 12 carbon atoms and at least one carbon to carbon double bond. Alkenyl groups may also be substituted at any available point of attachment. Exemplary substituents for alkenyl groups include those listed above for alkyl groups, and especially include $C_3$ to $C_7$ cycloalkyl groups such as cyclopropyl, cyclopentyl and cyclohexyl, which may be further substituted with, for example, amino, oxo, hydroxyl, etc.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkenyl groups include those listed above for alkyl groups such as amino, alkylamino, etc.

The numbers in the subscript after the symbol "C" define the number of carbon atoms a particular group can contain. For example "$C_1$ to $C_6$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_1$ to $C_6$ alkyl" can also refer to $C_1$ to $C_6$ alkylene which bridges two groups; examples include propane-1,3-diyl, butane-1,4-diyl, 2-methyl-butane-1,4-diyl, etc. "$C_2$ to $C_6$ alkyenyl means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_2$ to $C_6$ alkenyl" can also refer to $C_2$ to $C_6$ alkenediyl which bridges two groups; examples include ethylene-1,2-diyl(vinylene), 2-methyl-2-butene-1,4-diyl, 2-hexene-1,6-diyl, etc. "$C_2$ to $C_6$ alkynyl" means a straight or branched carbon chain having at least one carbon-carbon triple bond, and from two to six carbon atoms; examples include ethynyl, propynyl, butynyl, and hexynyl.

The term "acyl" herein alone or as part of another group refers to an alkyl group bonded through a carbonyl group or —C(O)R.

The term "alkoxy" herein alone or as part of another group denotes an alkyl group, preferably having from 1 to 6 carbon atoms, bonded through an oxygen atom, such as —OR, wherein R is the alkyl group.

The term "alkyloxycarbonyl" herein alone or as part of another group refers to —C(O)OR, wherein R is an alkyl group.

The term "arylalkyl" or "aralkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Preferred aryl groups contain from 6 to 14 carbon atoms in the rings. Aryl groups may optionally be substituted with one or more groups including, but not limited to halogen, such as Br, F, or Cl, alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol.

The term "amino" herein alone or as part of another group refers to —$NH_2$. An "amino" may optionally be substituted with one or two substituents (NR'R"), wherein R' and R" may be the same or different, such as alkyl, aryl, arylalkyl, alkenyl, alkynyl, heteroaryl, heteroarylalkyl, heterocycloalkyl, alkyl, heterocycloalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, or any of the alkyl or aryl substituents set out herein. In some embodiments, the amino groups are substituted with carboxyl or carbonyl to form N-acyl or N-carbamoyl derivatives.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, selected from the group consisting of halo, alkyl, substituted alkyl, wherein the substituents are defined as above for alkyl substituents, alkenyl, alkynyl, nitro, cyano, oxo (=O), hydroxy, alkoxy, thioalkyl, —$O_2H$, —C(=O)H, $CO_2$-alkyl, —C(=O)alkyl, keto, =N—OH, =N—O-alkyl, aryl, heteroaryl, heterocycloalkyl, a five or six membered ketal (i.e. 1,3-dioxolane or 1,3-dioxane), —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" are independently selected from hydrogen, alkyl, substituted alkyl, and cycloalkyl, or R' and R" together form a heterocycloalkyl or heteroaryl ring.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —$C_2H$, —C(=O)H, —$CO_2$-alkyl, C(=O)alkyl, phenyl, benzyl, phenylethyl, phenyloxy, phenylthio, cycloalkyl, substituted cycloalkyl, heterocycloalkyl, heteroaryl, —NR'R", —C(=O)NR'R", —$O_2$NR'R", —C(=O)NR'R", —NR' $CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocycloalkyl or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which one of the carbon atoms in the ring is replaced by a heteroatom selected from O, S or N, and in which up to three additional carbon atoms may be replaced by said heteroatoms. The term "heterocycloalkyl" herein alone or as part of another group refers to a stable, saturated, or partially unsaturated monocyclic ring system containing 5 to 7 ring members of carbon atoms and other atoms selected from nitrogen, sulfur and/or oxygen. A heterocyclic ring may be a 5, 6 or 7-membered monocyclic ring and contain one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocycloalkyl groups include piperazine, piperidine, morpholine, homomorpholine, thiomorpholine, pyrrolidine, and azetidine.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

The term "anticancer" agent includes alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Additionally, the compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

The above other therapeutic agents, when employed in combination with the compounds of the present invention, can be used, for example, in those amounts indicated in the Physicians' Desk Reference (PDR) or as otherwise determined by one of ordinary skill in the art.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species, including humans, cowes, horses, dogs, and cats.

The phrase "pharmaceutically effective" is intended to qualify the amount of each agent, which will achieve the goal of improvement in disorder severity and the frequency of incidence over treatment of each agent by itself, while avoiding adverse side-effects typically associated with alternative therapies. For example, effective anticancer agents prolong the survivability of the patient, inhibit the rapidly proliferating cell growth associated with the neoplasm, or effect a regression of the neoplasm.

The phrase "pharmaceutically acceptable salt(s)", or "salt" as used herein, unless otherwise indicated, includes salts of acidic or basic groups which may be present in the compounds of formulas I and II. The compounds of the present invention that are basic in nature are capable of forming a wide variety of salts with various inorganic and organic acids. Accordingly, compounds as defined by the term "Formula I, II or III" include both the free base and salt forms. The acids that may be used to prepare pharmaceutically acceptable acid addition salts of such basic compounds of formulas I and II are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, mesylate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Compounds of the present invention may contain one or more additional asymmetric carbon atoms and therefore exist in two or more stereoisomeric forms. The present invention includes the individual stereoisomers of the compounds of the present invention where appropriate, the individual tautomeric forms thereof, together with mixtures thereof.

Separation of diastereoisomers may be achieved by conventional techniques, e.g. by fractional crystallization, chromatography or H.P.L.C. of a stereoisomeric mixture of a compound of Formula I, II and/or II, or a suitable salt or derivative thereof. An individual enantiomer of a compound of the formula I, II or III may also be prepared from a corresponding optically pure intermediate or by resolution, such as by H.P.L.C. of the corresponding racemate using a suitable chiral support or by fractional crystallization of the diastereoisomeric salts formed by reaction of the corresponding racemate with a suitable optically active acid or base, as appropriate.

The phrase "gene amplification," as used herein means the selective synthesis of a DNA fragment that results in multiple copies of the Met gene or fragment of the chromosome in which Met is encoded.

The phrase "activated Met mutation" as used herein means a selective change in the DNA sequence of Met resulting in a Met protein that is constitutively (i.e., permanently) phosphorylated.

The phrase "HGF stimulation," as used herein means the ability of a HGF to bind its cognate receptor (Met) in such a way as to activate the receptor that results in a phenotypic response. In the case of Met, this can be cellular proliferation, motility, differentiation and/or survival.

More specifically, the compounds of Formulae I, II and III are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including melanoma, seminoma, teratocarcinoma, osteosarcoma, xenoderoma pigmentosum, keratoctanthoma, thyroid follicular cancer and Kaposi's sarcoma.

Due to the key role protein kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formulas I and II as modulators of apoptosis, will be useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formulas I and II may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formulas I and II may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formulas I and II may also be useful in inhibiting tumor angiogenesis and metastasis.

The compounds of this invention may also be useful in combination (administered together or sequentially) with known anti-cancer agents or treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2).

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients or carriers which are suitable for the manufacture of tablets. These excipients or carriers may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formulas I and II may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the present invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of Formulas I and II may also be administered sequentially with known anticancer or cytotoxic agents when a combination formulation is inappropriate. The invention is not limited in the sequence of administration; compounds of Formulas I and II may be administered either prior to or after administration of the known anticancer or cytotoxic agent(s).

Compounds of the present invention may generally be prepared according to the following Schemes 1 to 3. Tautomers, and solvates (e.g., hydrates) the compounds of Formula I, II, or III (which include salts) are also within the scope of the present invention. Methods of solvation are generally known in the art. Accordingly, the compounds of the instant invention may be in the free or hydrate form, and may be obtained by methods exemplified by the following schemes.

The appropriately substituted commercially available carboxylic acid 1 can be treated with oxalyl chloride in methylene chloride to generate the desired acid chloride 2 (Scheme 1). Treatment of compound 2 with an appropriately substituted heterocycle, such as 3-amino-1-(4-fluorophenyl)pyridin-2(1H)-one (3) (see Example 1B) can provide the amide 4. Coupling of amide 4 with 1H-pyrrolo[2,3-b]pyridin-4-ol (5, Thibault, C. et al. *Org. Lett.* 2003, 5, 5023-5025, herein incorporated by reference in its entirety) in the presence of a base, such as potassium carbonate in DMF can furnish the desired product 6.

SCHEME 1

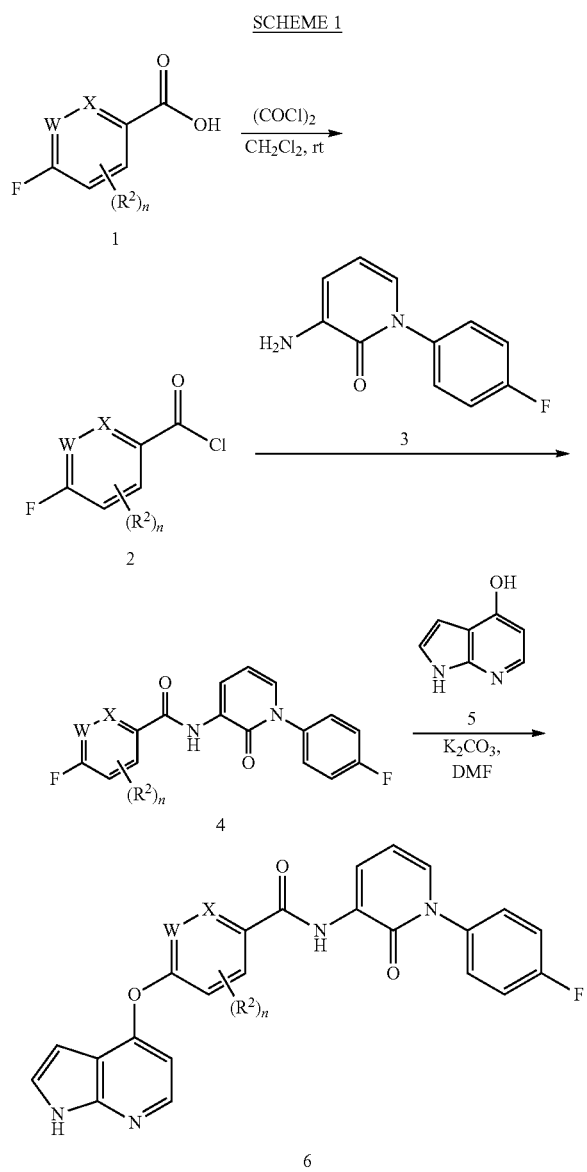

Alternatively, the desired analogues can be prepared according to Scheme 2. The leaving group (Lg), such as a halogen (or triflate) of a heterocycle (A, whereby open positions may be optionally substituted) 7 can be displaced with a substituted alcohol or phenol 8 (commercially available or easily prepared by one skilled in the art) in the presence of a base (i.e., cesium carbonate) to provide ether 9 (Scheme 2). Groups A-Lg can be prepared according to the general procedures outlined in, for example, Hunt, J. T. et al. WO 00/071129; Hunt, J. T. et al. *J. Med. Chem.* 2004, 47, 4054-4059; Leftheris, K et al. WO 02/040486; Mastalerz, H. et al. WO 03/042172; Dyckman, A. et al. WO 03/091229; Vite, G. D. et al. WO 04/054514; Salvati, M. E. et al. WO 03/082208; Thibault, C. et al. *Org. Lett.* 2003, 5, 5023-5025; Zhang, Z. et al. *J. Org. Chem.* 2002, 67, 2345-2347; Itoh, T. et al. *J. Heterocyclic Chem.* 1982, 19, 513-517; Tedder, M. E. et al. *Bioorg. Med. Chem. Lett.* 2004, 14, 3165-3168; Dorn, H. et al. *J. Prakt. Chem.* 1982, 324, 557; Sanghvi, Y. S. et al. *J. Med. Chem.* 1989, 32, 945-951; Temple, C. Jr. et al. *J. Org. Chem.* 1972, 37, 3601-3604; Hurst, J. et al. EP119774; Hurst, J. et al. EP151962; Ward, R. W. et al. EP152910; Luzzio, M. J. et al. WO 01/094353; Marx, M. A. et al. WO 03/000194; Boschelli, D. H. et al. WO 04/048386; He, M. et al. WO 05/021554; Barker, J. M. et al. *J. Chem. Res., Synopses* 1986, 4, 122-123, the disclosures of which are herein incorporated by reference. Treatment of carboxylic acid 9 with an appropriately substituted heterocycle, such as 3-amino-1-(4-fluorophenyl)pyridin-2(1H)-one (3) under standard peptide coupling conditions, such as O-(7-azabenzotriazol-1-yl)-N,N,N'-N'-tetramethyluronium hexafluorophosphate (HATU) in DMF at elevated temperatures can provide the amide 10.

SCHEME 2

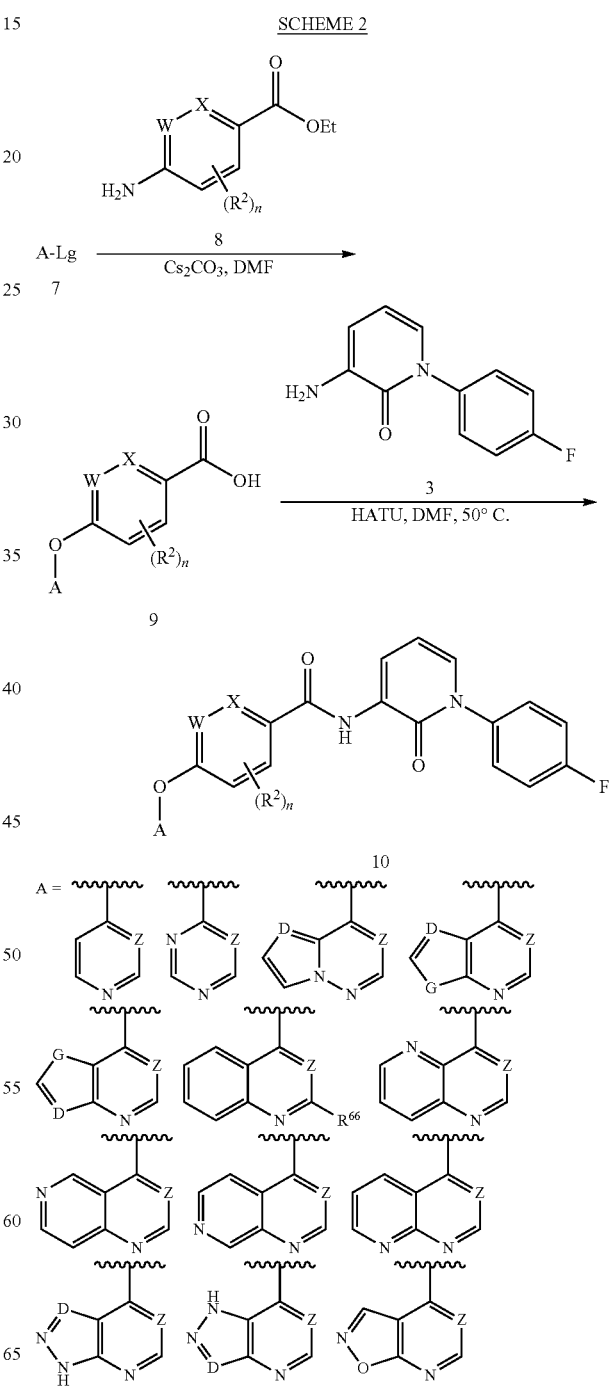

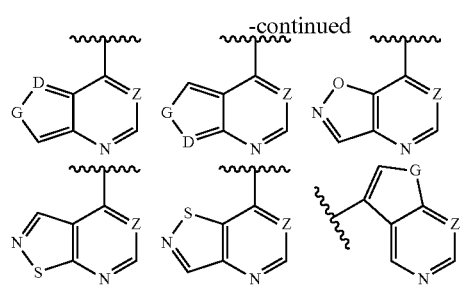

where Lg=leaving group, such as halogen and groups D, G, and Z are defined as above.

In cases where A=

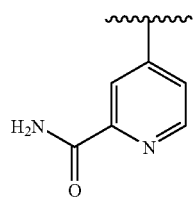

the desired aminopyridine analogue 12 can be prepared from Hofmann rearrangement of carboxamide 11 with either bis-(trifluoroacetoxy)-iodobenzene, pyridine and water in DMF or bromine, potassium hydroxide in water (Scheme 3).

Assays

The pharmacological properties of the compounds of this invention may be confirmed by a number of pharmacological assays. The exemplified pharmacological assays which follow have been carried out with the compounds according to the invention.

| Met Kinase assay | |
|---|---|
| Reagents | Substrate Mix Final Concentration |
| Stock Solution | |
| Tris-HCl, (1M, pH 7.4) | 20 mM |
| MnCl$_2$ (1M) | 1 mM |
| DTT(1M) | 1 mM |
| BSA (100 mg/ml) | 0.1 mg/ml |
| polyGlu$_4$/tyr (10 mg/ml) | 0.1 mg/mL |
| ATP (1 mM) | 1 μM |
| γ-ATP (10 μCi/μl) | 0.2 μCi/ml |
| Buffer | Enzyme mix |
| 20 ul 1M DTT | 4 ul GST/Met enzyme(3.2 mg/ml) = 10 ng/rxn |
| 200 ul 1M Tris-HCL, pH 7.4 | qs 12 ml Buffer |
| 20 ul 100 mg/ml BSA | |
| qs 20 ml H$_2$O | |

Incubation mixtures employed for the Met kinase assay contain the synthetic substrate polyGlu:Tyr, (4:1), ATP, ATP-γ-$^{33}$P and buffer containing Mn$^{++}$ and/or Mg$^{++}$, DTT, BSA,

SCHEME 3

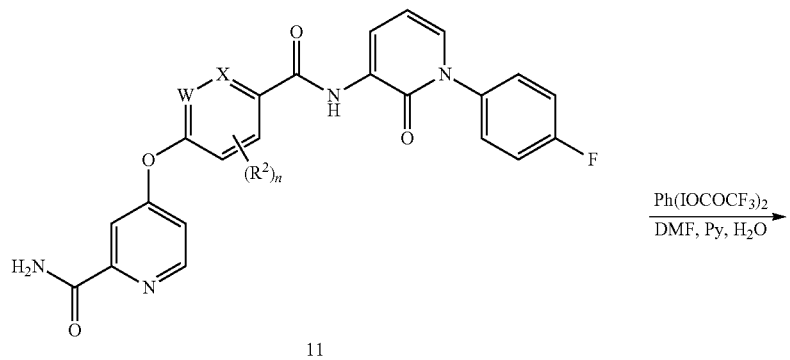

11

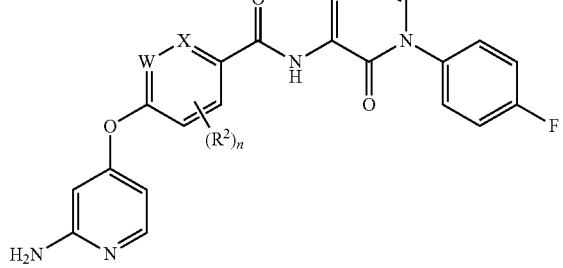

12 and Tris buffer. Reactions are incubated for 60 minutes at 27° C. and stopped by the addition of cold trichloroacetic acid (TCA) to a final concentration 4%. TCA precipitates are collected onto GF/C unifilter plates (Packard Instrument Co., Meriden, Conn.) using a Filtermate universal harvester (Packard Instrument Co., Meriden, Conn.) and the filters are quantitated using a TopCount 96-well liquid scintillation counter (Packard Instrument Co., Meriden, Conn.). Dose response curves are generated to determine the concentration required to inhibit 50% of kinase activity ($IC_{50}$). Compounds are dissolved at 10 mM in dimethyl sulfoxide (DMSO) and evaluated at six concentrations, each in quadruplicate. The final concentration of DMSO in the assay is 1%. $IC_{50}$ values are derived by non-linear regression analysis and have a coefficient of variance (SD/mean, n=6)=16%.

Preferred compounds of the invention inhibit the Met kinase enzyme with $IC_{50}$ values between 0.01 to 100 μM. More preferred compounds have $IC_{50}$ values less than 1.0 μM, and most preferably, less than about 0.5 μM.

The following examples and preparations describe the manner and process of making and using the invention and are illustrative rather than limiting. It should be understood that there may be other embodiments which fall within the spirit and scope of the invention as defined by the claims appended hereto.

EXAMPLES

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP) HPLC was performed using a Phenomenex Luna C18 S5 4.6 mm×50 mm column or a YMC S5 ODS 4.6×50 mm column. In each case a 4 min linear gradient (from 100% A: % 0 B to 0% A: 100% B) was used with the following mobile phase system: A=90% $H_2O$/MeOH+0.2% $H_3PO_4$; B=90% MeOH/$H_2O$+0.2% $H_3PO_4$ at flow rate=4 mL/min and detection at 220 nm.

Preparative Reverse Phase (RP) HPLC was performed with a linear gradient elution using $H_2O$/MeOH mixtures buffered with 0.1% trifluoroacetic acid and detection at 220 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min).

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for commonly used reagents: Boc or BOC: t-butyl carbamate; Fmoc: 9H-fluorenylmethyl carbamate; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxytris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT: room temperature; $t_R$: retention time; h: hour(s); min: minute(s); PyBrOP: bromotripyrrolidinophosphonium hexafluorophosphate; TBTU: O-(1H-benzotriazol-1-yl)-N,N,N',N'-tetramethyluronium tetrafluoroborate; DMAP: 4-N,N-dimethylaminopyridine; HOBt: hydroxybenzotriazole; HATU: O-(7-azabenzotriazol-1-yl)-N,N,N',N'-tetramethyluronium hexafluorophosphate; DIBAL-H: diisobutylaluminum hydride; Na(OAc)$_3$BH: sodium triacetoxyborohydride; HOAc: acetic acid; TFA: trifluoroacetic acid; LiHMDS: lithium bis(trimethylsilyl)amide; m-CPBA: m-chloro: 3-chloroperbenzoic acid; AIBN: 2,2'-azobisisobutyronitrile; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; Et$_2$O: diethyl ether.

Example 1

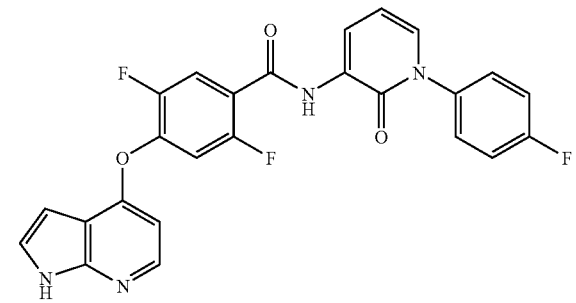

4-(1H-Pyrrolo[2,3-b]pyridin-4-yloxy)-2,5-difluoro-N-(1-(4-fluorophenyl)-2-oxo-1,2-dihydropyridin-3-yl)benzamide, Trifluoroacetic acid salt

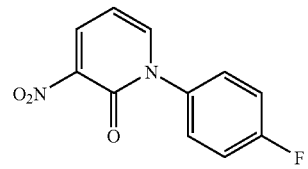

A) 1-(4-Fluorophenyl)-3-nitropyridin-2(1H)-one

To a solution of 2-hydroxy-3-nitropyridine (Aldrich, 3.0 mmol, 420 mg) in 1,4-dioxane (20 mL), were added 4-fluorophenyl boronic acid (Combi-block, 6.0 mmol, 840 mg), copper(I) acetate (Aldrich, 4.5 mmol, 815 mg) and pyridine (2 mL). The reaction was heated at 80° C. for 20 h. After cooling to room temperature, 30 mL of cold water was added. The solid formed was collected by filtration, washed with ammonium hydroxide and water, and dried under vacuum to give the desired product (610 mg, 87% yield) as a solid. MS(ESI$^+$) m/z 235.30 (M+H)$^+$.

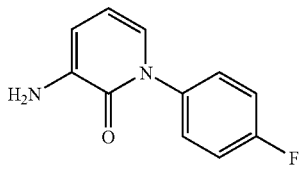

B) 3-Amino-1-(4-fluorophenyl)pyridin-2(1H)-one

To a solution of 1-(4-fluorophenyl)-3-nitropyridin-2(1H)-one (610 mg, 2.6 mmol) in THF (50 mL) and MeOH (50 mL), were added ammonium chloride (695 mg, 13.0 mmol, EMD) and Zn dust (850 mg, 13.0 mmol, Aldrich). The reaction mixture was stirred at room temperature for 3 h, diluted with 200 mL of EtOAc and filtered through a pad of Celitee. The filtrate was concentrated in vacuo to give the desired product (530 mg, 100% yield) as a brown solid. MS(ESI+) m/z 205.29 (M+H)$^+$.

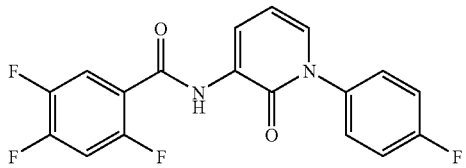

C) 2,4,5-Trifluoro-N-(1-(4-fluorophenyl)-2-oxo-1,2-dihydropyridin-3-yl)benzamide To a solution of 2,4,5-trifluorobenzoic acid (Aldrich, 704 mg, 4.0 mmol) in dichloromethane (20 mL), was added oxalyl chloride (Aldrich, 0.70 mL, 8.0 mmol) dropwise, followed by two drops of DMF. The reaction mixture was stirred at room temperature for 2 h, and concentrated in vacuo. Toluene (20 mL) was added and the reaction mixture was evaporated in vacuo to remove the excess oxalyl chloride. The residue was dissolved in dichloromethane (20 mL). Half of this acid chloride solution was added to a mixture of 3-amino-1-(4-fluorophenyl)pyridin-2(1H)-one (306 mg, 1.5 mmol) in dichloromethane (5 mL) and TEA (0.5 mL, Aldrich) at 0° C. The reaction mixture was stirred at room temperature for 1 h. The precipitate that formed was collected by filtration, and washed with methanol, to afford the desired product (363 mg, 67% yield) as a solid. MS(ESI$^+$) m/z 363.25 (M+H)$^+$.

D) 4-(1H-Pyrrolo[2,3-b]pyridin-4-yloxy)-2,5-difluoro-N-(1-(4-fluorophenyl)-2-oxo-1,2-dihydropyridin-3-yl)benzamide, Trifluoroacetic acid salt To a solution of compound 1H-pyrrolo[2,3-b]pyridin-4-ol (0.1 mmol, 13.4 mg, prepared generally according to the procedures outlined by Thibault, C. et al. *Org. Lett.* 2003, 5, 5023-5025, the disclosure of which is incorporated by reference, in DMF (1 mL) was added cesium carbonate (Aldrich, 0.25 mmol, 81 mg). The mixture was stirred at room temperature for 0.5 h. To this mixture was added 2,4,5-trifluoro-N-(1-(4-fluorophenyl)-2-oxo-1,2-dihydropyridin-3-yl)benzamide (36 mg, 0.1 mmol). The reaction mixture was heated at 60° C. for 8 h. After the reaction mixture was cooled to room temperature, 2 mL of cold water was added. The reaction mixture was extracted with EtOAc (3×20 mL). The organic extracts were dried with MgSO$_4$, concentrated in vacuo, and purified by preparative HPLC. The desired fractions were combined, concentrated in vacuo, and lyophilized to dry to give the title compound (trifluoroacetic acid salt, 10.0 mg, 21% yield) as a white solid. $^1$H NMR (CD$_3$OD) δ 8.61 (d, 1H, J=5.7 Hz), 8.26 (d, 1H, J=6.6 Hz), 8.02 (dd, 1H, J=11.0, 6.6 Hz), 7.51 (d, 1H, J=3.9 Hz), 7.29-7.25 (m, 3H), 7.36 (d, 1H, J=6.6 Hz), 7.25 (t, 2H, J=8.8 Hz), 6.90 (d, 1H, J=6.6 Hz), 6.60 (d, 1H, J=3.3 Hz), 6.50 (t, 1H, J=7.2 Hz); MS(ESI$^+$) m/z 477.22 (M+H)$^+$.

Example 2

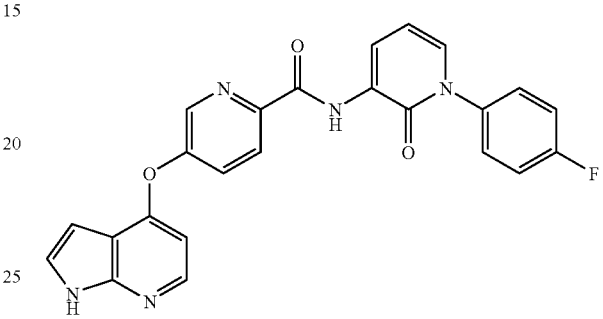

5-(1H-Pyrrolo[2,3-b]pyridin-4-yloxy)-N-(1-(4-fluorophenyl)-2-oxo-1,2-dihydropyridin-3-yl)picolinamide Prepared in a similar manner as Example 1 (18.5 mg, 42% yield) except 5-fluoropyridine-2-carboxylic acid (Synchem OHG) was used. $^1$H NMR (DMSO-d$_6$) δ 10.65 (s, 1H), 8.65 (d, 1H, J=2.8 Hz), 8.50 (d, 1H, J=7.7 Hz), 8.21 (d 1H, J=8.2 Hz), 8.18 (d 1H, J=6.5 Hz), 7.76 (dd, 1H, J=8.3, 2.7 Hz), 7.57-7.54 (m, 2H), 7.46 (d, 1H, J=5.0 Hz), 7.43 (d, 1H, J=3.3 Hz), 7.38 (t, 2H, J=8.8 Hz), 6.74 (d, 1H, J=4.9 Hz), 6.47 (t, 1H, J=7.2 Hz), 6.20 (d, 1H, J=3.8 Hz); MS(ESI+) m/z 442.25 (M+H)$^+$.

Example 3

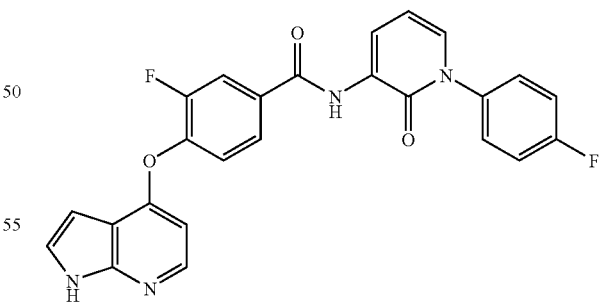

4-(1H-Pyrrolo[2,3-b]pyridin-4-yloxy)-3-fluoro-N-(1-(4-fluorophenyl)-2-oxo-1,2-dihydropyridin-3-yl)benzamide, Trifluoroacetic acid salt Prepared in a similar manner as Example 1 (5.5 mg, 12% yield) except 3,4-difluorobenzoic acid (Aldrich) was used. $^1$H NMR (CD$_3$OD) δ 8.47 (d, 1H, J=7.2 Hz), 8.20 (d, 1H, J=6.1

Hz), 7.91 (d, 1H, J=11.0 Hz), 7.84 (d, 1H, J=9.4 Hz), 7.50 (t, 1H, J=8.3 Hz), 7.45-7.40 (m, 3H), 7.31 (d, 1H, J=6.6 Hz), 7.21 (t, 2H, J=8.8 Hz), 6.78 (d, 1H, J=6.6 Hz), 6.54 (d, 1H, J=3.8 Hz), 6.45 (t, 1H, J=7.2 Hz); MS(ESI$^+$) m/z 459.20 (M+H)$^+$.

Example 4

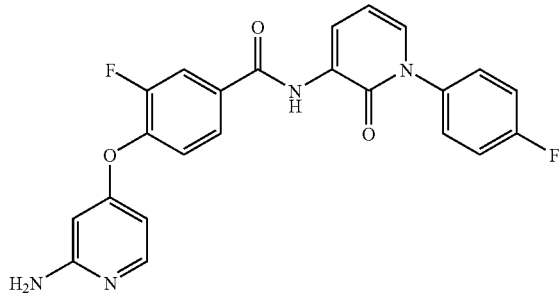

4-(2-Aminopyridin-4-yloxy)-3-fluoro-N-(1-(4-fluorophenyl)-2-oxo-1,2-dihydropyridin-3-yl)benzamide, Trifluoroacetic acid salt

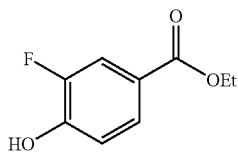

A) Ethyl 3-fluoro-4-hydroxybenzoate

To a solution of 3-fluoro-4-hydroxybenzoic acid (Aldrich, 4.0 mmol, 624 mg) in ethanol (10 mL), was added thionyl chloride (2 mL, Aldrich). The reaction mixture was heated at 80° C. for 4 h, and concentrated in vacuo to remove the solvent and excess thionyl chloride to afford the desired product (736 mg, 100% yield) as a white solid. MS(ESI$^+$) m/z 185.33 (M+H)$^+$.

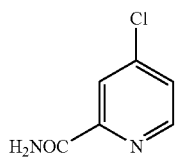

B) 4-Chloropicolinamide

A heterogeneous mixture of 4-chloropicolinic acid (TCI America, 5.4 g, 34.2 mmol, 1.0 eq) and thionyl chloride (30 mL) was heated at 80° C. for 2 h. The reaction mixture was cooled to room temperature and concentrated in vacuo. The residue was treated with an ammonia in MeOH solution (7N, 45 mL) in an ice bath and the reaction mixture was stirred for 15 minutes. The ice bath was then removed and the reaction was warmed to room temperature and then stirred for 3 h. The reaction mixture was concentrated in vacuo and the residue purified by recrystallization from EtOAc to afford the product (5.14 g, 96%) as a solid. $^1$H NMR (DMSO-d$_6$) δ 8.61-8.63 (m, 1H), 8.21 (m, 1H), 8.03-8.04 (m, 1H), 7.76-7.83 (m, 2H); MS(ESI$^+$) m/z 157 (M+H)$^+$.

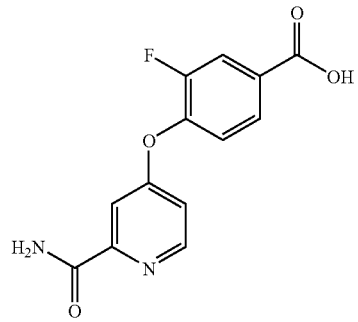

C) 4-(2-Carbamoylpyridin-4-yloxy)-3-fluorobenzoic acid

To a solution of ethyl 3-fluoro-4-hydroxybenzoate (2.0 mmol, 368 mg) in DMF (5 mL), were added cesium carbonate (Aldrich, 6.0 mmol, 1.95 g) and 4-chloropicolinamide (2.0 mmol, 312 mg). The reaction mixture was heated at 130° C. for 20 h. After cooling to room temperature, 5 mL of cold water was added. The aqueous solution was washed with EtOAc (2×20 mL), and neutralized with 1N HCl to pH 3-4. The precipitate that formed was collected by filtration, washed with water, and dried under vacuum to give the desired product (164 mg, 27% yield). MS(ESI$^+$) m/z 277.32 (M+H)$^+$.

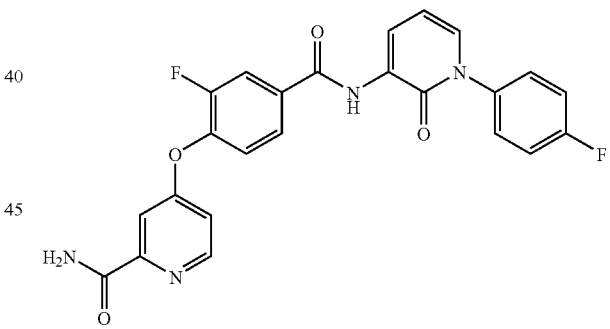

D) 4-(2-Fluoro-4-((1-(4-fluorophenyl)-2-oxo-1,2-dihydropyridin-3-yl)carbamoyl)phenoxy)picolinamide To a solution of 4-(2-carbamoylpyridin-4-yloxy)-3-fluorobenzoic acid (0.3 mmol, 83 mg) in DMF (2 mL), were added HATU (Perspective Biosystems, 0.45 mmol, 171 mg), 3-amino-1-(4-fluorophenyl)pyridin-2(1H)-one (0.3 mmol, 61.2 mg) and DEEA (Aldrich, 0.2 mL). The reaction mixture were heated at 50° C. for 5 h. After cooling to room temperature, 5 mL of methanol was added. The product was purified by preparative HPLC. The desired fractions were combined, neutralized to pH 7-8 with aq. K$_2$HPO$_4$, and concentrated in vacuo. The precipitate that formed was collected by filtration, rinsed with water, and dried under vacuum to give the desired product (78 mg, 57% yield). MS(ESf+) m/z 463.25 (M+H)$^+$.

E) 4-(2-Aminopyridin-4-yloxy)-3-fluoro-N-(1-(4-fluorophenyl)-2-oxo-1,2-dihydropyridin-3-yl)benzamide, Trifluoroacetic acid salt To a solution of 4-(2-fluoro-4-((1-(4-fluorophenyl)-2-oxo-1,2-dihydropyridin-3-yl)carbamoyl)phenoxy)picolinamide (15 mg, 0.032 mmol) in DMF (0.5 mL) at room temperature, were added pyridine (0.1 mL), water (0.05 mL), and [bis(trifluoroacetoxyl)-iodo]benzene (21.5 mg, 0.05 mmol, Aldrich). The reaction mixture was stirred at 0° C. for 4 h, and was then quenched by the addition of 1 mL of methanol and 1 mL of water. The reaction mixture was purified by preparative HPLC. The desired fractions were combined, concentrated in vacuo and lyophilized to give the title compound (trifluoroacetic acid salt, 10 mg, 72% yield) as a white solid. $^1$H NMR (CD$_3$OD) δ 8.45 (d, 1H, J=6.1 Hz), 7.90 (d, 1H, J=11.0 Hz), 7.83 (d, 1H, J=8.8 Hz), 7.77 (d, 1H, J=7.2 Hz), 7.45 (t, 1H, J=8.3 Hz), 7.41-7.39 (m, 2H), 7.32 (d, 1H, J=7.2 Hz), 7.21 (t, 2H, J=8.3 Hz), 6.62 (dd, 1H, J=7.2, 2.2 Hz), 6.45 (t, 1H, J=7.2 Hz), 6.17 (d, 1H, J=2.2 Hz); MS(ESI$^+$) m/z 435.22 (M+H)$^+$.

We claim:

1. A compound having the following formula III:

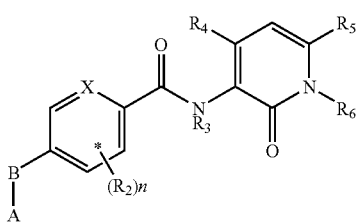

wherein
each $R^2$ is independently H, halo, cyano, NO$_2$, OR$^7$, NR$^8$R$^9$, an/or C$_1$ to C$_6$ alkyl;
n is 1 to 3;
X is —CR$^2$ or N;
R$^3$ is H;
R$^4$ and R$^5$ are independently H, halo, haloalkyl, NO$_2$, cyano, —OR$^{14}$, —NR$^{15}$R$^{16}$, and/or C$_1$ to C$_6$ alkyl;
R$^6$ is H, C$_1$ to C$_6$ alkyl, phenyl, or phenyl substituted with halo;
R$^7$, R$^8$, and R$^9$ are independently H and/or C$_1$ to C$_6$ alkyl;
R$^{14}$, R$^{15}$, and R$^{16}$ are independently H and/or C$_1$ to C$_6$ alkyl;
B is O;
A is:

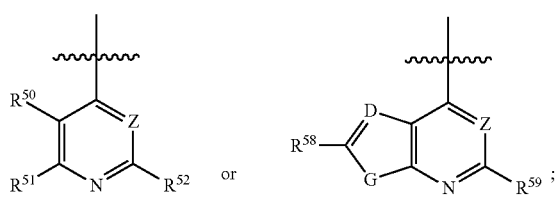

Z is CR$^{108}$;
G is NR$^{106}$;
D is CR$^{107}$;
R$^{106}$ is H;
R$^{50}$, R$^{51}$, R$^{52}$, R$^{58}$, R$^{59}$, R$^{107}$, and R$^{108}$ are independently H, halo, haloalkyl, —NO$_2$, cyano, —OR$^{109}$, and/or —NR$^{110}$R$^{111}$; and
R$^{100}$, R$^{110}$, and R$^{111}$ are independently H and/or alkyl.

2. The compound according to claim 1 wherein R$^5$ is H.

3. The compound according to claim 1 wherein X is —CR$^2$ and each R$^2$ is H and/or halo.

4. The compound according to claim 3 wherein each R$^2$ is H and/or F.

5. The compound according to claim 1 wherein R$^6$ is phenyl substituted with halo.

6. The compound according to claim 5 wherein R$^6$ is phenyl substituted with a halo substituent.

7. The compound according to claim 6 wherein R$^6$ is fluorophenyl.

8. The compound according to claim 1 wherein X is —CR$^2$.

9. The compound according to claim 1 wherein X is N.

10. The compound according to claim 1 wherein A is

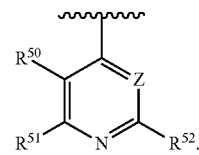

11. The compound according to claim 10 wherein A is an aminopyridine.

12. The compound according to claim 1 wherein:
each R$^2$ is independently H and/or halo;
n is 1 to 2;
R$^6$ is fluorophenyl;
A is:

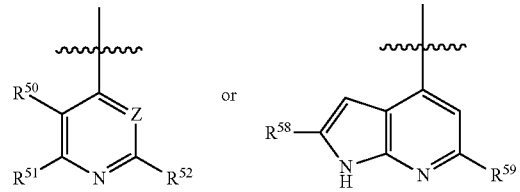

wherein
Z is —CH.

13. The compound according to claim 12 wherein X is —CH.

14. The compound according to claim 12 wherein X is —CH or N; R$^6$ is fluorophenyl; R$^3$ is H; and R$^{50}$, R$^{52}$, R$^{58}$, and R$^{59}$ are each H; and R$^{51}$ is H or amino.

15. The compound according to claim 12 selected from the group consisting of:
   4-(1H-Pyrrolo[2,3-b]pyridin-4-yloxy)-2,5-difluoro-N-(1-(4-fluorophenyl)-2-oxo-1,2-dihydropyridin-3-yl)benzamide, trifluoroacetic acid salt;
   5-(1H-Pyrrolo[2,3-b]pyridin-4-yloxy)-N-(1-(4-fluorophenyl)-2-oxo-1,2-dihydropyridin-3-yl)picolinamide;
   4-(1H-Pyrrolo[2,3-b]pyridin-4-yloxy)-3-fluoro-N-(1-(4-fluorophenyl)-2-oxo-1,2-dihydropyridin-3-yl)benzamide, trifluoroacetic acid salt; and
   4-(2-Aminopyridin-4-yloxy)-3-fluoro-N-(1-(4-fluorophenyl)-2-oxo-1,2-dihydropyridin-3-yl)benzamide, trifluoroacetic acid salt.

16. A pharmaceutical composition comprising a compound according to claim 1 in a pharmaceutically acceptable carrier.

* * * * *

UNITED STATES PATENT AND TRADEMARK OFFICE
CERTIFICATE OF CORRECTION

PATENT NO. : 7,880,004 B2
APPLICATION NO. : 11/521035
DATED : February 1, 2011
INVENTOR(S) : Borzilleri et al.

Page 1 of 1

It is certified that error appears in the above-identified patent and that said Letters Patent is hereby corrected as shown below:

In the Claims:
Claim 1, col. 31, lines 23-32, delete "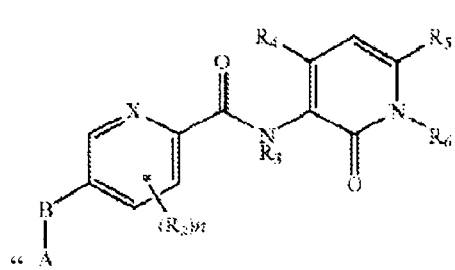" and insert -- 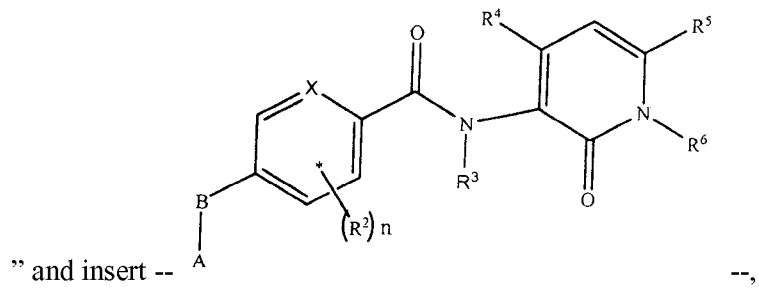 --, therefor; and Claim 1, col. 31, line 65, delete "$R^{100}$" and insert -- $R^{109}$ --, therefor.

Signed and Sealed this
Twenty-fifth Day of October, 2011

David J. Kappos
*Director of the United States Patent and Trademark Office*